(12) United States Patent
Choi

(10) Patent No.: US 6,538,147 B1
(45) Date of Patent: Mar. 25, 2003

(54) ORGANOCOPPER PRECURSORS FOR CHEMICAL VAPOR DEPOSITION

(76) Inventor: Hyungsoo Choi, 1712 Brighton Ct., Champaign, IL (US) 61822

( * ) Notice: Subject to any disclaimer, the term of this patent is extended or adjusted under 35 U.S.C. 154(b) by 0 days.

(21) Appl. No.: 09/744,619

(22) PCT Filed: Aug. 6, 1999

(86) PCT No.: PCT/KR99/00438

§ 371 (c)(1),
(2), (4) Date: Jan. 25, 2001

(87) PCT Pub. No.: WO00/08225

PCT Pub. Date: Feb. 17, 2000

(30) Foreign Application Priority Data

Aug. 6, 1998 (KR) .............................. 98-32069

(51) Int. Cl.⁷ ............................. C07F 1/08; C23C 16/18
(52) U.S. Cl. ................... 556/110; 556/113; 556/114; 427/250; 427/123; 427/124
(58) Field of Search ................. 427/250, 123, 427/124, 314; 556/9, 117, 12, 110, 113, 114

(56) References Cited

U.S. PATENT DOCUMENTS

| 5,098,516 | A |   | 3/1992 | Norman et al. |         |
|-----------|---|---|--------|---------------|---------|
| 5,441,766 | A | * | 8/1995 | Choi et al.   | 427/250 |
| 5,441,786 | A |   | 8/1995 | Choi et al.   |         |
| 5,767,301 | A |   | 6/1998 | Senzaki et al.|         |

OTHER PUBLICATIONS

"Selectivity and Copper Chemical Vapor Deposition," Dubois et al. J. Electrochem. Soc., vol. 139, No. 11, Nov. 1992, pp 3295–3299.

"Copper metalorganic chemical vapor deposition reactions of hexafluoroacetylacetonate Cu(I) vinyltrimethylsilane and bis (hexafluoroacetylacetonate) Cu(II) adsorbed on titanium nitride," J. Vac. Sci. Technol. A 11(1) Jan./Feb. 1993, pp. 66–77.

"Chemistry of copper (I) B–diketonate complexes" Chi et al., Journal of Organometallic Chemistry, 449 (1993) pp. 181–189.

"Copper(I) tert–Butyl 3–Oxobutanoate Complexes as Precursors for Chemical Vapor Deposition of Copper," Choi et al., Beckman Institute for Advanced Science and Technology, University of Illinois at Urbana, vol. 10, No. 9, pp. 2326–2328. 1998.

* cited by examiner

*Primary Examiner*—Bret Chen
(74) *Attorney, Agent, or Firm*—Ohlandt, Greeley, Ruggiero & Perle, L.L.P.

(57) ABSTRACT

The present invention provides a copper precursor according to the formula $(R^3COOCR^2COR^1)Cu^{+1}\{L\}_x$, where x is 1, 2 or 3 and L is a neutral ligand. The precursors in the present invention, which are low melting solids or distillable liquids with high volatility and thermal stability, can be vaporized without decomposition and used to deposit high quality copper films. The improved stability of the copper compounds in the present invention enables them to reproducibly produce selective copper films on metallic or electrically conductive surfaces.

51 Claims, No Drawings

ORGANOCOPPER PRECURSORS FOR CHEMICAL VAPOR DEPOSITION

BACKGROUND OF THE INVENTION

1. Field of the Invention

The present invention relates to syntheses and utilization of new copper compounds as precursors for chemical vapor deposition to obtain high-quality copper films.

2. Description of the Prior Art

Chemical vapor deposition (CVD) processes have several advantages over physical vapor deposition (PVD) processes, such as the ability of conformal coverage and the possibility of selective deposition, to deposit copper and other metal films. To fabricate desirable materials by CVD processes, it is important to identify precursors which satisfy several requirements. The precursors should be vaporized easily and be thermally, stable at the temperatures at which vaporization occurs and yet can deposit desirable films at low, substrate temperatures.

The need for high performance interconnection materials increases as device feature sizes shrink and device density increases. Copper is expected to provide an alternative to CVD-aluminum or CVD-tungsten for metallization of ultra large scale integrated (ULSI) devices due to its low resistivity (1.67 $\mu\Omega$cm for Cu, 2.65 $\mu\Omega$cm for Al and 5.7 $\mu\Omega$cm for W), high electromigration resistance and high melting point (1083° C. for Cu, 660° C. for Al and 3410° C. for W). Low interconnect resistivity allows for faster devices.

Copper CVD precursors are divided into two groups, i.e., Cu(I) and Cu(II) complexes. The precursors in the former group are quite volatile and show low deposition temperatures, but are highly, sensitive to heat and oxygen. The latter precursors are rather stable, but are isolated as solids with high melting points and thus require high deposition temperatures. It is not uncommon that impurities such as carbon or oxygen are incorporated during the thermal CVD process when using certain organometallic precursors. For instance, ($\eta^5$-$C_5H_5$)Cu(PMe$_3$) and (tert-BuO)Cu(PMe$_3$) produce copper films via thermal decomposition reactions leading to incorporation of impurities. To avoid such a problem, it is necessary to tailor an organocopper precursor to deposit copper without decomposition of the ligands.

(hfac)CuL, where hfac=1,1,1,5,5,5-hexafluoro-2,4-pentanedionate and L=Lewis base, have been the most studied copper precursors to date because they can deposit copper via thermal disproportionation reaction. Especially (hfac)Cu(tmvs), where tmvs=trimethylvinylsilane, has attracted much attention since it is a liquid with reasonably high vapor pressure. Other copper compounds such as (hfac)CuL, where L=1,5-cyclooctadiene (COD), alkyne or trialkylphosphine, are either solids or liquids with a low vapor pressure. Although (hfac)Cu(tmvs) has been the most utilized copper precursor, its stability is not satisfactory for the selective growth of copper films with reproducibility (L. H. Dubois, et al., J. Electrochem. Soc., 1992, 139, 3295). In addition, a study (V. M. Donnelly, et al., Vac. Sci. Technol. A, 1993, 11, 66) demonstrated that the chemical vador deposition reaction of (hfac)Cu(tmvs) under ultra high vacuum conditions produced contamination by carbon and fluorine in the deposited films. This implies a possibility of fluorine contamination during the deposition process under certain conditions. Copper compounds of fluorinated ($\beta$-diketonates other than (hfac)CuL, such as (fod)CuL, where fod=2,2-dimethyl-6,6,7,7,8,8-heptafluoro-3,5-octanedionate (fod), or (tfac)CuL, where tfac=1,1,1-trifluoro-2,4-pentanedionate, were reported not to exhibit sufficient thermal stability to be used as CVD precursors (K. M. Chi, et al., J. Organomet. Chem., 1993, 449, 181). Therefore, a precursor with high volatility and stability, which contains no fluorinated ligands, is more desirable for the deposition of copper by CVD.

Copper compounds of acetoacetate derivatives which contain no fluorinated ligands were reported as CVD precursors. They were reported to be volatile and to deposit copper films at low substrate temperatures (H. Choi, et al., U.S. Pat. No. 5,441,766). Cu(II) acetoacetate derivatives in the report were found to be attractive since they were volatile without employing fluorinated ligands and deposited copper films at temperatures below 200° C. However, they were solids with high melting points and were incapable of selective deposition of copper. On the other hand, the Cu(I) acetoacetate derivatives deposited copper films at relatively low temperatures via disproportionation reaction. However, few are practical for use as CVD precursors since they are either solids or liquids with a low vapor pressure or they have an extremely low thermal stability (i.e. their decomposition temperature is within a few degrees of their vaporization temperature). A limited claim was made to the alkylphosphite family of Cu(I) acetoacetate precursors demonstrated to deposit copper at low temperatures (H. Choi, Korean Patent Application No. 1998-32069). This is an expansion of those claims to include other recent works presented by Choi et al. (H. Choi, et al. Chem. Mater. 1998, 2326).

SUMMARY OF THE INVENTION

The object of the present invention is to provide new Cu(I) CVD precursors which contain no fluorinated ligands and are capable of depositing high-quality copper at low deposition temperatures.

The precursors according to the invention include: ($R^3$COOC$R^2$CO$R^1$)Cu$^{+1}$\{L\}$_x$, where x is 1, 2 or 3, L is a neutral ligand which is a phosphine, phosphite or an unsaturated hydrocarbon, and $R^1$ and $R^3$ are each independently $C_1$–$C_9$ alkyl or aryl groups and $R^2$ may be H, F or $C_1$–$C_9$ alkyl or aryl groups, wherein $R^3$ may also be an alkylsilane group, \{—Si($R^4$)($R^5$)($R^6$)\}, wherein $R^4$, $R^5$ and $R^6$ independently may be $C_{1-C9}$ alkyl or aryl or alkoxy (—OR where R is $C_1$–$C_9$ alkyl or aryl) groups attached to silicon. The precursors in the present invention, which are low melting solids or distillable liquids with high volatility and thermal stability, can be vaporized without decomposition and used to deposit high-quality copper films. The improved stability of the copper compounds in the present invention enables them to reproducibly produce selective copper films on metallic or electrically conductive surfaces.

Further objects and advantages of the invention will become apparent through reading the remainder of the specification.

DETAILED DESCRIPTION OF THE INVENTION

According to the invention, the general formula of the organocopper precursor is ($R^3$COOC$R^2$CO$R^1$)Cu$^{+1}$\{L\}$_x$ where x is 1, 2 or 3;

$R^1$ and $R^3$ are each independently $C_1$–$C_9$ alkyl or aryl groups and $R^2$ may be H, F or $C_1$–$C_9$ alkyl or aryl groups, wherein $R^3$ may also be an alkylsilane group, \{—Si($R^4$)($R^5$)($R^6$)\}, wherein $R^4$, $R^5$ and $R^6$ independently may be $C_1$–$C_9$ alkyl or aryl or alkoxy (—OR where R is $C_1$–$C_9$ alkyl or aryl) groups attached to silicon; and L is a neutral ligand which can be a phosphine or phosphite ligand, $\{P(R^7)(R^8)(R^9)\}$ wherein $R^7$, $R^8$ and $R^9$ are each independently hydroxy or $C_1$–$C_9$ alkyl or aryl or alkoxy (—OR where R is $C_1$–$C_9$ alkyl or aryl) groups wherein if at least one of $R^7$, $R^8$ or $R^9$ groups is an alkoxy group the electron donating ability of oxygen in the phosphite ligand strengthens the bond between the Cu and the phosphite ligand resulting in enhanced stability of the compound.

The neutral ligand, L, may also be an unsaturated hydrocarbon described as $(R^{10})(R^{11})$—C=C—$(R^{12})(R^{13})$ containing at least one carbon-carbon double bond, wherein $R^{10}$, $R^{11}$, $R^{12}$ and $R^{13}$ are each independently H, F, $C_1$–$C_9$ alkyl or aryl or an alkylsilane group, $\{-Si(R^{14})(R^{15})(R^{16})\}$, wherein $R^{14}$, $R^{15}$ and $R^{16}$ independently may be $C_1$–$C_9$ alkyl or aryl or alkoxy (—OR where R is $C_1$–$C_9$ alkyl or aryl) groups attached to silicon, and any combination of $R^{10}$, $R^{11}$, $R^{12}$ or $R^{13}$ may be joined together to form at least one $C_4$–$C_{16}$ cycloaliphatic ring containing at least one carbon-carbon double bond.

The neutral ligand, L, may also be an unsaturated hydrocarbon described as $(R^{17})$—C≡C—$(R^{18})$ containing at least one carbon-carbon triple bond. wherein $R^{17}$ and $R^{18}$ are each independently H, F, $C_1$–$C_9$ alkyl or aryl or an alkylsilane group, $\{-Si(R^{14})(R^{15})(R^{16})\}$, wherein $R^{14}$, $R^{15}$ and $R^{16}$ independently may be $C_1$–$C_9$ alkyl or aryl or alkoxy (—OR where R is $C_1$–$C_9$ alkyl or aryl) groups attached to silicon, and $R^{17}$ and $R^{18}$ may be joined together to form at least one $C_4$–$C_{16}$ cycloaliphatic ring containing at least one carbon-carbon triple bond.

The charged ligand, $(R^3COOCR^2COR^1)$, is an acetoacetate derivative, and is most preferably $^tBuCOOCHCOCH_3$ or tert-butylacetoacetate. The precursor can be synthesized by the following method:

Reaction of sodium acetoacetate derivative with the neutral ligand adduct of cuprous chloride.

$$CuCl + x\{L\} \rightarrow \{L\}x \cdot CuCl \quad (1)$$

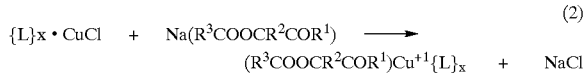

$$\{L\}x \cdot CuCl + Na(R^3COOCR^2COR^1) \longrightarrow$$
$$(R^3COOCR^2COR^1)Cu^{+1}\{L\}_x + NaCl \quad (2)$$

The Cu(I) compounds, (acetoacetate derivative)Cu$^{+1}$ (neutral ligand), synthesized in the manner described above, are obtained as distillable liquids or low melting solids with high volatility and exhibit improved thermal stability and deposition characteristics. It is important to judiciously choose the appropriate ligand as a Lewis base to achieve higher thermal stability of the precursor. The improved stability of the copper compounds in the present invention enables them to produce selective copper films over a wide temperature range. The copper films thus formed using the present invention are free from carbon-, oxygen- or fluorine-containing impurities since there are no fluorine atoms in the precursor and the films are deposited via disproportionation reaction instead of a thermal decomposition reaction.

The precursors obtained in the manner described above were subjected to a chemical vapor deposition apparatus comprising a precursor vessel, a heated Pyrex reactor and a vacuum system to produce copper thin films. The vaporized precursor is injected into the reactor with or without hydrogen gas while the precursor vessel is maintained in the temperature range of 15–100 ° C. When the precursor reaches the substrate, a thermally induced disproportionation reaction deposits copper on the substrate. Silicon (Si), or coated silicon (SiO$_2$/Si or TiN/Si) wafers are used as substrates, but any substrate suitable for the CVD process may be used. Depositions are conducted over the temperature range of 100–300 ° C. The reactor is maintained at 0.1 to 10 mmHg during the deposition reaction, and the deposition rate is dependent upon the reaction conditions used.

The compounds in the present invention are suitable for the production of high-purity copper films due to the fact that there are no fluorine atoms in the precursors and that the deposition of copper occurs via disproportionation reaction as shown in eq. 3. The resulting volatile Cu(II) acetoacetate derivative and neutral ligand evolved from the disproportionation reaction are passed out of the deposition zone intact.

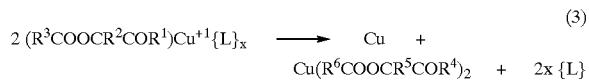

$$2\ (R^3COOCR^2COR^1)Cu^{+1}\{L\}_x \longrightarrow Cu + Cu(R^6COOCR^5COR^4)_2 + 2x\{L\} \quad (3)$$

Another advantage of the present invention is that it allows selective deposition on metallic or electrically conductive surfaces with wide temperature window. Copper films were deposited on Si or TiN/Si wafers as low as 120° C. while no deposition was observed on SiO$_2$/Si at 200° C. The favored deposition of copper on Si or TiN/Si surfaces can be explained by the catalytic effect of metallic or electrically conductive surfaces to promote the disproportionation of the Cu(I) compounds. Therefore, the selectivity is expected to improve with the thermal stability of the precursor. The improved thermal stability of the precursors in the present invention is very important for the selective deposition of copper with reproducibility.

The thermal stability of Cu(I) acetoacetate derivatives in the present invention was improved remarkably by employing such materials as trimethylphosphite (TMP), 1,5-dimethyl-1,5-cyclooctadiene (1,5-DMCOD) or bistrimethylsilylacetylene (BTMSA) as new ligands so that the resulting adducts can be used as practical CVD precursors.

Scanning electron microscopy (SEM) image of the deposited copper films using the present invention showed good surface morphology and step coverage on vias of ULSI substrates. No impurities such as carbon or oxygen were detected from the X-ray photoelectron spectra (XPS) of the deposited films. The resistivities of the as-deposited films ranged from 1.8 to 2.5 μΩcm.

PREFERRED EMBODIMENT OF THE INVENTION

The present invention will be illustrated in greater detail by way of following examples. The examples are presented for illustrative purpose only and should not be construed as limiting the invention, which are properly delineated in the claims.

All reactions and subsequent manipulations involving organometallic reagents were performed under an inert atmosphere (for example, helium, argon or nitrogen) using Schlenk-type glassware and glove box techniques. All reagents were purchased from Aldrich Chemical Co. (Milwaukee, Wis.). All solvents were purchased from Baxter Healthcare Co. (Muskegon, Mich.) and freshly distilled from Na under nitrogen. Trimethylphosphite, 1,5-dimethyl-1,5-cyclooctadien, bistrimethylsilylacetylene and tert-butylacetoacetate (Hbtac) were freshly distilled under nitrogen. Infrared spectra were recorded on either a BioRad FTS60A FT-IR spectrometer or a Perkin Elmer 1600 Series FT-IR spectrometer.

EXAMPLE 1

Synthesis of (tert-butylacetoacetate)copper (trimethylphosphite)

$P(OMe)_3$ (1.04 g, 8.4 mmol) was added to a diethylether solution (25 mL) of CuCl (0.79 g, 8.0 mmol) at room temperature to form {TMP}.CuCl. The resulting solution was stirred for 15 min and then cooled to −78° C. A solution of Na(btac) (1.56 g, 8.6 mmol) was added slowly with constant stirring to the reaction mixture using a syringe. The reaction mixture was slowly warmed to room temperature over 4 hrs. The solvent was removed in vacuo and replaced with 25 ml pentane. After stirring for 30 min, the resulting reaction mixture was filtered through a medium porosity glass frit to remove the solids. The reaction flask was washed with pentane (2×5 mL) and the filtrates were collected. The solvent was removed in vacuo to leave a liquid product. The crude product was vacuum distilled. The boiling point is 33° C. at 0.1 torr and the material decomposes at 120° C.

EXAMPLE 2

Synthesis of (tert-butylacetoacetate)copper(1,5-dimethyl-1,5-cyclooctadiene)

1,5-dimethyl-1,5-cyclooctadiene (1.14 g, 8.4 mmol) was added to a tetrahydrofuran solution (25 mL) of CuCl (0.79 g, 8.0 mmol) at room temperature to form {1,5-DMCOD}.CuCl. The resulting solution was stirred for 30 min and then cooled to −40° C. A solution of Na(btac) (1.56 g, 8.6 mmol) was added slowly with constant stirring to the reaction mixture using a syringe. The reaction mixture was slowly warmed to room temperature over 3 hrs. The solvent was removed in vacuo and replaced with 25 ml pentane. After stirring for 30 min, the resulting reaction mixture was filtered through a medium porosity glass frit to remove the solids. The reaction flask was washed with pentane (2×5 mL) and the filtrates were collected. The solvent was removed in vacuo to leave a solid product. The solvent was removed in vacuo to leave a liquid product. The product decomposed at 60° C.

EXAMPLE 3

Synthesis of (tert-butylacetoacetate)copper (bistrimethylsilylacetylene)

Bistrimethylsilylacetylene (1.43 g, 8.4 mmol) was added to a tetrahydrofuran solution (25 mL) of CuCl (0.79 g, 8.0 mmol) at room temperature to form {BTMSA}.CuCl. The resulting solution was stirred for 30 min and then cooled to −40° C. A solution of Na(btac) (1.56 g, 8.6 mmol) was added slowly with constant stirring to the reaction mixture using a syringe. The reaction mixture was slowly warmed to room temperature over 4 to 5 hrs. The solvent was removed in vacuo and replaced with 25 ml pentane. After stirring for 30 min, the resulting reaction mixture was filtered through a medium porosity glass frit to remove the solids. The reaction flask was washed with pentane (2×5 mL) and the filtrates were collected. The solvent was removed in vacuo to leave a solid product. The material melted and distilled at 58° C. when heated under reduced pressure (≅0.05 torr) and decomposed at 95° C.

EXAMPLE 4

Chemical Vapor Deposition of Copper Films

A silicon, a TiN-coated silicon, or a thermally grown $SiO_2$ on Si wafer was used as a substrate. Deposition was conducted in a glass reactor by feeding (tert-butylacetoacetate)copper(neutral ligand) with or without argon as a carrier gas. The wafer was heated to a temperature between 100° C. and 300° C. The total pressure of the system was maintained at 0.1 torr when no carrier gas was used. When argon gas was used as a carrier gas, the system was maintained at 3–10 torr. The temperature of the precursor vessel was maintained at 20–60° C. Copper films were deposited on Si or TiN substrates at temperatures as low as 120° C. while no deposition was observed on $SiO_2$ substrates at 200° C. This demonstrates the capability of the precursors in the present invention to deposit copper selectively over a wide temperature range. XPS spectra showed no carbon or oxygen impurities in the deposited film. SEM photos showed good step coverage and surface morphology of the deposited copper films on high-aspect-ratio ULSI substrates.

According to the present invention, thermally stable and volatile organocopper(I) compounds which produce high-quality copper under CVD conditions can be provided by coordinating the acetoacetate derivative and appropriate neutral ligands to copper(I). While these precursors are quite stable and deposit copper films free of carbon, oxygen and fluorine, several different ingredients can be added to enhance the stability of the precursor, adhesion properties or the deposition rate of copper. These additives can be blended with the precursor either directly or by addition to a vapor of the precursor during its introduction to a reactor. Addition of excess neutral ligand, L, can increase the stability of the material both during storage (i.e. longer shelf-life) and during vaporization. Further, the addition of excess acetoacetate derivative (i.e. $R^3COOCHR^2COR^1$) and/or water vapor either directly to the copper precursor or separately supplied to a reactor can enhance the deposition rate of copper. Finally, the use of hydrogen gas during deposition or as an anneal can lower the carbon or oxygen content.

What is claimed is:

1. A volatile solid or liquid copper precursor of composition $(R^3COOCR^2COR^1)Cu^{+1}(L)_x$ of the following formula,

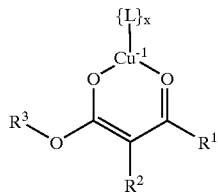

wherein:
    a) L is a neutral ligand and x is 2 or 3, and
    b) the charged ligand is an acetoacetate derivative where $R^1$ is $C_1$–$C_9$ alkyl or aryl groups, $R^2$ is H or $C_1$–$C_9$ alkyl or aryl groups, $R^3$ is $C_1$–$C_9$ alkyl or aryl groups, or an alkylsilane group of the formula {—Si($R^4$)($R^5$)($R^6$)}, wherein $R^4$, $R^5$ and $R^6$ independently are H, $C_1$–$C_9$ alkyl, aryl or alkoxy (—OR where R is $C_1$–$C_9$ alkyl or aryl) groups attached to silicon.

2. The precursor as in claim 1 where the neutral ligand L is a phosphine or phosphite, {P($R^7$)($R^8$)($R^9$)}, wherein $R^7$, $R^8$ and $R^9$ are each independently hydroxy or $C_1$–$C_9$ alkyl or aryl or alkoxy (—OR where R is $C_1$–$C_9$ alkyl or aryl) groups.

3. The precursor as in claim 2 wherein $R^1$ is methyl, $R^2$ is hydrogen and $R^3$ is butyl.

4. The precursor as in claim 2 wherein each $R^7$, $R^8$ and $R^9$ is methoxy.

5. The precursor as in claim 4 wherein $R^1$ is methyl, $R^2$ is hydrogen and $R^3$ is tert-butyl.

6. The precursor as in claim 1 where the neutral ligand L is an unsaturated hydrocarbon described as $(R^{10})(R^{11})-C=C-(R^{12})(R^{13})$ containing at least one carbon-carbon double bond, wherein $R^{10}$, $R^{11}$, $R^{12}$ and $R^{13}$ are each independently H, $C_1-C_9$ alkyl or aryl or an alkylsilane group, $\{-Si(R^{14})(R^{15})(R^{16})\}$, wherein $R^{14}$, $R^{15}$ and $R^{16}$ independently are H, $C_1-C_9$ alkyl or aryl or alkoxy $\{-OR$ where R is $C_1-C_9$ alkyl or aryl) groups attached to silicon, and any combination of $R^{10}$, $R^{11}$, $R^{12}$ or $R^{13}$ may be joined together to form at least one $C_4-C_{16}$ cycloaliphatic ring containing at least one carbon-carbon double bond.

7. The precursor as in claim 6 wherein $R^1$ is methyl, $R^2$ is hydrogen and $R^3$ is butyl.

8. The precursor as in claim 6 wherein the neutral ligand is 1,5-dimethyl-1,5-cyclooctadiene.

9. The precursor as in claim 8 wherein $R^1$ is methyl, $R^2$ is hydrogen and $R^3$ is tert-butyl.

10. The precursor as in claim 1 where the neutral ligand L is an unsaturated hydrocarbon described as $(R^{17})-C\equiv C-(R^{18})$ containing at least one carbon-carbon triple bond, wherein $R^{17}$ and $R^{18}$ are each independently H, $C_1-C_9$ alkyl or aryl or an alkylsilane group, $\{-Si(R^{14})(R^{15})(R^{16})\}$, wherein $R^{14}$, $R^{15}$ and $R^{16}$ independently are H, $C_1-C_9$ alkyl or aryl or alkoxy (—OR where R is $C_1-C_9$ alkyl or aryl) groups attached to silicon, and $R^{17}$ and $R^{18}$ may be joined together to form at least one $C_4-C_{16}$ cycloaliphatic ring containing at least one carbon-carbon triple bond.

11. The precursor as in claim 10 wherein $R^1$ is methyl, $R^2$ is hydrogen and $R^3$ is butyl.

12. A method of depositing copper on a substrate using the precursor as in claim 11 in the presence of water vapor.

13. The precursor as in claim 10 wherein the neutral ligand is bistrimethylsilylacetylene.

14. The precursor as in claim 13 wherein $R^1$ is methyl, $R^2$ is hydrogen and $R^3$ is tert-butyl.

15. A method of depositing copper on a substrate using the precursor as in claim 1 wherein the copper precursor is vaporized between the temperatures of 15–100° C. and transported to said substrate.

16. A method of depositing copper on a substrate using the precursor as in claim 1 wherein the copper precursor is vaporized and transported to said substrate in the presence of an inert carrier gas such as helium, nitrogen or argon as a method of transport.

17. A method of depositing copper on a substrate using the precursor as in claim 1 wherein the copper precursor is vaporized and transported to said substrate which is heated to a temperature between 100–300° C.

18. A method of depositing copper on a substrate using the precursor as in claim 1 wherein the copper precursor is vaporized and transported to a substrate in the presence of a partial pressure of water which is used to increase the deposition rate of copper.

19. A method of depositing copper on a substrate using the precursor as in claim 1 wherein the copper precursor includes an additive to create a blend, where the additive is an acetoacetate derivative ($R^3COOCHR^2COR^1$) of the following formula (a) or (b) used to facilitate the disproportionation reaction and to enhance the deposition rate of copper, where $R^1$ is $C_1-C_9$ alkyl or aryl groups, $R^2$ is H, or $C_1-C_9$ alkyl or aryl groups, $R^3$ is $C_1-C_9$ alkyl or aryl groups, or an alkylsilane group of the formula $\{-Si(R^4)(R^5)(R^6)\}$, wherein $R^4$, $R^5$ and $R^6$ independently are H, $C_1-C_9$ alkyl, aryl or alkoxy (—OR where R is $C_1-C_9$ alkyl or aryl) groups attached to silicon:

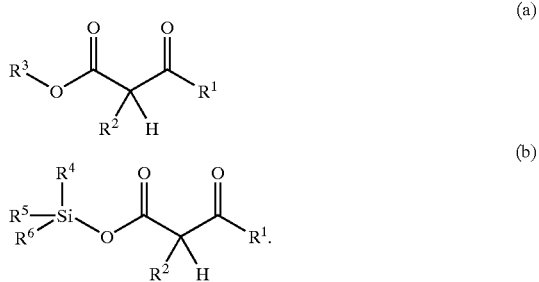

20. A method of depositing copper on a substrate using the precursor as in claim 1 wherein the copper precursor includes an additive to create a blend, where the additive is a phosphine or phosphite $\{P(R^7)(R^8)(R^9)\}$ used to prevent the material from prematurely decomposing during transportation and during heating wherein $R^7$, $R^8$ and $R^9$ are each independently hydroxy or $C_1-C_9$ alkyl or aryl or alkoxy (—OR where R is $C_1-C_9$ alkyl or aryl) groups.

21. A method of depositing copper on a substrate using the precursor as in claim 1 wherein the copper precursor includes an additive to create a blend, where the additive is an unsaturated hydrocarbon described as $(R^{10})(R^{11})-C=C-(R^{12})(R^{13})$ containing at least one carbon-carbon double bond wherein $R^{10}$, $R^{11}$, $R^{12}$ and $R^{13}$ are each independently H, $C_1-C_9$ alkyl or aryl or an alkylsilane group, $\{-Si(R^{14})(R^{15})(R^{16})\}$, wherein $R^{14}$ and $R^{15}$ and $R^{16}$ independently are H, $C_1-C_9$ alkyl or aryl or alkoxy (—OR where R is $C_1-C_9$ alkyl or aryl) groups attached to silicon, and any combination of $R^{10}$, $R^{11}$, $R^{12}$ or $R^{13}$ may be joined together to form at least one $C_4-C_{16}$ cycloaliphatic ring containing at least one carbon-carbon double bond.

22. A method of depositing copper on a substrate using the precursor as in claim 1 wherein the copper precursor includes an additive to create a blend, where the additive is an unsaturated hydrocarbon described as $(R^{17})-C\equiv C-(R^{18})$ containing at least one carbon-carbon triple bond wherein $R^{17}$ and $R^{18}$ are each independently H, $C_1-C_9$ alkyl or aryl or an alkylsilane group, $\{-Si(R^{14})(R^{15})(R^{16})\}$, wherein $R^{14}$, $R^{15}$ and $R^{16}$ independently are H, $C_1-C_9$ alkyl or aryl or alkoxy (—OR where R is $C_1-C_9$ alkyl or aryl) groups attached to silicon, and $R^{17}$ and $R^{18}$ may be joined together to form at least one $C_4-C_{16}$ cycloaliphatic ring containing at least one carbon-carbon triple bond.

23. A method of depositing copper on a substrate using the precursor as in claim 1 wherein the copper precursor is vaporized and transported to a substrate in the presence of a partial pressure of hydrogen gas during deposition to decrease the impurity content of the resultant Cu film.

24. A method of depositing copper on a substrate using the precursor as in claim 1 wherein the copper precursor is vaporized and transported to a substrate followed by being subjected to a thermal anneal using a partial pressure of hydrogen gas to decrease the impurity content of the resultant Cu film.

25. A method of depositing copper on a substrate using the precursor as in claim 1 wherein the copper precursor is vaporized and transported to a substrate for the selective deposition of Cu on a metallic or electrically conductive substrate.

26. A volatile solid or liquid copper precursor of composition $(R^3COOCR^2COR^1)Cu^{+1}(L)_x$ of the following formula,

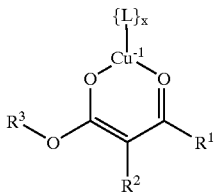

wherein:
a) L is a neutral ligand selected from the group consisting of:
  i) a phosphite, $\{P(R^7)(R^8)(R^9)\}$, wherein $R^7$, $R^8$ and $R^9$ are each independently hydroxy or alkoxy (—OR where R is $C_1$–$C_9$ alkyl or aryl) groups;
  ii) an unsaturated hydrocarbon described as $(R^{10})(R^{11})$—C=C—$(R^{12})(R^{13})$ containing at least one carbon-carbon double bond, wherein $R^{10}$, $R^{11}$, $R^{12}$ and $R^{13}$ are each independently H, $C_1$–$C_9$ alkyl or aryl or an alkylsilane group, $\{$—$Si(R^{14})(R^{15})(R^{16})\}$, wherein $R^{14}$, $R^{15}$ and $R^{16}$ independently are H, $C_1$–$C_9$ alkyl, aryl or alkoxy {—OR where R is $C_1$–$C_9$ alkyl or aryl) groups attached to silicon, and any combination of $R^{10}$, $R^{11}$, $R^{12}$ or $R^{13}$ may be joined together to form at least one $C_4$–$C_{16}$ cycloaliphatic ring containing at least one carbon-carbon double bond, wherein the unsaturated hydrocarbon is not cyclooctadiene;
  iii) an unsaturated hydrocarbon described as $(R^{17})$—C≡C—$(R^{18})$ containing at least one carbon-carbon triple bond, wherein $R^{17}$ and $R^{18}$ are each independently H, $C_1$–$C_9$ alkyl, aryl or an alkylsilane group, $\{$—$Si(R^{14})(R^{15})(R^{16})\}$, wherein $R^{14}$, $R^{15}$ and $R^{16}$ independently are H, $C_1$–$C_9$ alkyl, aryl or alkoxy (—OR where R is $C_1$–$C_9$ alkyl or aryl) groups attached to silicon, and $R^{17}$ and $R^{18}$ may be joined together to form at least one $C_4$–$C_{16}$ cycloaliphatic ring containing at least one carbon-carbon triple bond, wherein when $R^{17}$ is H, $R^{18}$ cannot be ethyl;
b) x is 1; and
c) the charged ligand is an acetoacetate derivative where $R^1$ is $C_1$–$C_9$ alkyl or aryl groups, $R^2$ is H or $C_1$–$C_9$ alkyl or aryl groups, $R^3$ is $C_1$–$C_9$ alkyl or aryl groups, or an alkylsilane group of the formula $\{$—$Si(R^4)(R^5)(R^6)\}$, wherein $R^4$, $R^5$ and $R^6$ independently are H, $C_1$–$C_9$ alkyl, aryl or alkoxy (—OR where R is $C_1$–$C_9$ alkyl or aryl) groups attached to silicon.

27. The precursor as in claim 26 wherein $R^1$ is methyl, $R^2$ is hydrogen and $R^3$ is butyl.

28. The precursor as in claim 26 wherein L is a phosphite, $\{P(R^7)(R^8)(R^9)\}$, wherein $R^7$, $R^8$ and $R^9$ are each independently hydroxy or alkoxy (—OR where R is $C_1$–$C_9$ alkyl or aryl) groups.

29. The precursor as in claim 28 wherein each $R^7$, $R^8$ and $R^9$ is methoxy.

30. The precursor as in claim 29 wherein $R^1$ is methyl, $R^2$ is hydrogen and $R^3$ is tert-butyl.

31. The precursor as in claim 28 wherein $R^1$ is methyl, $R^2$ is hydrogen and $R^3$ is butyl.

32. The precursor as in claim 26 wherein L is an unsaturated hydrocarbon described as $(R^{10})(R^{11})$—C=C—$(R^{12})(R^{13})$ containing at least one carbon-carbon double bond, wherein $R^{10}$, $R^{11}$, $R^{12}$ and $R^{13}$ are each independently H, $C_1$–$C_9$ alkyl, aryl or an alkylsilane group, $\{$—$Si(R^{14})(R^{15})(R^{16})\}$, wherein $R^{14}$, $R^{15}$ and $R^{16}$ independently are H, $C_1$–$C_9$ alkyl, aryl or alkoxy {—OR where R is $C_1$–$C_9$ alkyl or aryl) groups attached to silicon, and any-combination of $R^{10}$, $R^{11}$, $R^{12}$ or $R^{13}$ may be joined together to form at least one $C_4$–$C_{16}$ cycloaliphatic ring containing at least one carbon-carbon double bond wherein the unsaturated hydrocarbon is not a cyclooctadiene.

33. The precursor as in claim 32 wherein $R^1$ is methyl, $R^2$ is hydrogen and $R^3$ is butyl.

34. The precursor as in claim 32 wherein the neutral ligand is 1,5-dimethyl-1,5-cyclooctadiene.

35. The precursor as in claim 34 wherein $R^1$ is methyl, $R^2$ is hydrogen and $R^3$ is tert-butyl.

36. The precursor as in claim 26 wherein L is an unsaturated hydrocarbon described as $(R^{17})$—C≡C—$(R^{18})$ containing at least one carbon-carbon triple bond, wherein $R^{17}$ and $R^{18}$ are each independently H, $C_1$–$C_9$ alkyl or aryl or an alkylsilane group, $\{$—$Si(R^{14})(R^{15})(R^{16})\}$, wherein $R^{14}$, $R^{15}$ and $R^{16}$ independently are H, $C_1$–$C_9$ alkyl, aryl or alkoxy (—OR where R is $C_1$–$C_9$ alkyl or aryl) groups attached to silicon, and $R^{17}$ and $R^{18}$ may be joined together to form at least one $C_4$–$C_{16}$ cycloaliphatic ring containing at least one carbon-carbon triple bond, wherein when $R^{17}$ is H, $R^{18}$ cannot be ethyl.

37. The precursor as in claim 36 wherein $R^1$ is methyl, $R^2$ is hydrogen and $R^3$ is butyl.

38. A method of depositing copper on a substrate using the precursor as in claim 37 in the presence of water vapor.

39. The precursor as in claim 36 wherein the neutral ligand is bistrimethylsilylacetylene.

40. The precursor as in claim 39 wherein $R^1$ is methyl, $R^2$ is hydrogen and $R^3$ is tert-butyl.

41. A method of depositing copper on a substrate using the precursor as in claim 26 wherein the copper precursor is vaporized between the temperatures of 15–100° C. and transported to said substrate.

42. A method of depositing copper on a substrate using the precursor as in claim 26 wherein the copper precursor is vaporized and transported to said substrate in the presence of an inert carrier gas such as helium, nitrogen or argon as a method of transport.

43. A method of depositing copper on a substrate using the precursor as in claim 26 wherein the copper precursor is vaporized and transported to said substrate which is heated to a temperature between 100–300° C.

44. A method of depositing copper on a substrate using the precursor as in claim 26 wherein the copper precursor is vaporized and transported to a substrate in the presence of a partial pressure of water which is used to increase the deposition rate of copper.

45. A method of depositing copper on a substrate using the precursor as in claim 26 wherein the copper precursor includes an additive to create a blend, where the additive is an acetoacetate derivative $(R^3COOCHR^2COR^1)$ of the following formula (a) or (b) used to facilitate the disproportionation reaction and to enhance the deposition rate of copper, where $R^1$ is $C_1$–$C_9$ alkyl or aryl groups, $R^2$ is H or $C_1$–$C_9$ alkyl or aryl groups, $R^3$ is $C_1$–$C_9$ alkyl or aryl groups, or an alkylsilane group of the formula $\{$—$Si(R^4)(R^5)(R^6)\}$, wherein $R^4$, $R^5$ and $R^6$ independently are H, $C_1$–$C_9$ alkyl, aryl or alkoxy (—OR where R is $C_1$–$C_9$ alkyl or aryl) groups attached to silicon;

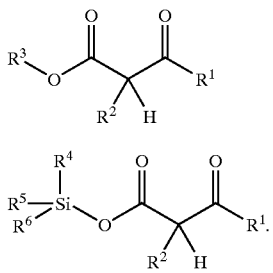

46. A method of depositing copper on a substrate using the precursor as in claim 26 wherein the copper precursor includes an additive to create a blend, where the additive is a phosphite $\{P(R^7)(R^8)(R^9)\}$ used to prevent the material from prematurely decomposing during transportation and during heating wherein $R^7$, $R^8$ and $R^9$ are each independently hydroxy or alkoxy (—OR where R is $C_1$–$C_9$ alkyl or aryl) groups.

47. A method of depositing copper on a substrate using the precursor as in claim 26 wherein the copper precursor includes an additive to create a blend, where the additive is an unsaturated hydrocarbon described as $(R^{10})(R^{11})$—C═C—$(R^{12})(R^{13})$ containing at least one carbon-carbon double bond wherein $R^{10}$, $R^{11}$, $R^{12}$ and $R^{13}$ are each independently H, $C_1$–$C_9$ alkyl or aryl or an alkylsilane group, $\{-Si(R^{14})(R^{15})(R^{16})\}$, wherein $R^{14}$ and $R^{15}$ and $R^{16}$ independently are H, $C_1$–$C_9$ alkyl or aryl or alkoxy (—OR where R is $C_1$–$C_9$ alkyl or aryl) groups attached to silicon, and any combination of $R^{10}$, $R^{11}$, $R^{12}$ or $R^{13}$ may be joined together to form at least one $C_4$–$C_{16}$ cycloaliphatic ring containing at least one carbon-carbon double bond.

48. A method of depositing copper on a substrate using the precursor as in claim 26 wherein the copper precursor includes an additive to create a blend, where the additive is an unsaturated hydrocarbon described as $(R^{17})$—C≡C—$(R^{18})$ containing at least one carbon-carbon triple bond wherein $R^{17}$ and $R^{18}$ are each independently H, $C_1$–$C_9$ alkyl or aryl or an alkylsilane group, $\{-Si(R^{14})(R^{15})(R^{16})\}$, wherein $R^{14}$, $R^{15}$ and $R^{16}$ independently are H, $C_1$–$C_9$ alkyl or aryl or alkoxy (—OR where R is $C_1$–$C_9$ alkyl or aryl) groups attached to silicon, and $R^{17}$ and $R^{18}$ may be joined together to form at least one $C_4$–$C_{16}$ cycloaliphatic ring containing at least one carbon-carbon triple bond.

49. A method of depositing copper on a substrate using the precursor as in claim 26 wherein the copper precursor is vaporized and transported to a substrate in the presence of a partial pressure of hydrogen gas during deposition to decrease the impurity content of the resultant Cu film.

50. A method of depositing copper on a substrate using the precursor as in claim 26 wherein the copper precursor is vaporized and transported to a substrate followed by being subjected to a thermal anneal using a partial pressure of hydrogen gas to decrease the impurity content of the resultant Cu film.

51. A method of depositing copper on a substrate using the precursor as in claim 26 wherein the copper precursor is vaporized and transported to a substrate for the selective deposition of Cu on a metallic or electrically conductive substrate.

* * * * *